(12) United States Patent
Chang et al.

(10) Patent No.: US 11,939,432 B2
(45) Date of Patent: *Mar. 26, 2024

(54) AMINO ACID-MODIFIED POLYMER FOR ADHESION PREVENTION AND APPLICATION THEREOF

(71) Applicant: PROVIEW-MBD BIOTECH CO., LTD., Taipei (TW)

(72) Inventors: Yu-Chia Chang, Taipei (TW);
Yunn-Kuen Chang, New Taipei (TW);
Wen-Yen Huang, Taipei (TW);
Ging-Ho Hsiue, Hsinchu (TW);
Hsieh-Chih Tsai, Taipei (TW);
Shuian-Yin Lin, Zhubei (TW);
Nai-Sheng Hsu, Taoyuan (TW);
Tzu-Yu Lin, Taipei (TW)

(73) Assignee: PROVIEW-MBD BIOTECH CO., LTD., Taipei (TW)

( * ) Notice: Subject to any disclaimer, the term of this patent is extended or adjusted under 35 U.S.C. 154(b) by 167 days.

This patent is subject to a terminal disclaimer.

(21) Appl. No.: 17/239,133

(22) Filed: Apr. 23, 2021

(65) Prior Publication Data

US 2021/0332193 A1  Oct. 28, 2021

Related U.S. Application Data

(60) Provisional application No. 63/014,756, filed on Apr. 24, 2020.

(51) Int. Cl.
*C08G 81/00* (2006.01)
*A61K 31/337* (2006.01)
(Continued)

(52) U.S. Cl.
CPC ............ *C08G 81/00* (2013.01); *A61K 31/337* (2013.01); *A61K 47/34* (2013.01); *A61L 31/041* (2013.01);
(Continued)

(58) Field of Classification Search
CPC ..... C08G 81/00; C08G 2650/58; A61K 47/34
See application file for complete search history.

(56) References Cited

U.S. PATENT DOCUMENTS 4,141,973 A    2/1979  Balazs
4,188,373 A    2/1980  Krezanoski
(Continued)

FOREIGN PATENT DOCUMENTS

WO    WO 2010/037044    *  4/2010
WO    WO 2013/040417    *  3/2013

OTHER PUBLICATIONS

EU Search Report in Application No. 21170042.2 dated Aug. 27, 2021.

*Primary Examiner* — Noble E Jarrell
(74) *Attorney, Agent, or Firm* — Maschoff Brennan

(57) ABSTRACT

Synthetic amino acid-modified polymers and methods of making the same and using the same are disclosed. The synthetic amino acid-modified polymers possess distinct thermosensitive, improved water-erosion resistant, and enhanced mechanical properties, and are suitable of reducing or preventing formation of postoperative tissue adhesions. Additionally, the amino acid-modified polymers can also be used as a vector to deliver pharmaceutically active agents.

18 Claims, 6 Drawing Sheets

(51) Int. Cl.
*A61K 47/34* (2017.01)
*A61L 31/04* (2006.01)
*A61L 31/06* (2006.01)
*A61L 31/16* (2006.01)
*C08L 71/02* (2006.01)

(52) U.S. Cl.
CPC .............. *A61L 31/06* (2013.01); *A61L 31/16* (2013.01); *C08L 71/02* (2013.01); *A61L 2300/216* (2013.01); *A61L 2300/416* (2013.01); *A61L 2300/424* (2013.01)

(56) References Cited

U.S. PATENT DOCUMENTS

| | | |
|---|---|---|
| 4,474,751 A | 10/1984 | Haslam et al. |
| 4,478,822 A | 10/1984 | Haslam et al. |
| 9,327,049 B2 | 5/2016 | Kim et al. |
| 9,895,446 B2 | 2/2018 | Simmons et al. |
| 10,105,387 B2 | 10/2018 | Jung et al. |
| 2009/0196844 A1 | 8/2009 | Choi et al. |
| 2015/0335749 A1 | 11/2015 | Schieker et al. |
| 2017/0202871 A1 | 7/2017 | Jung et al. |
| 2019/0375892 A1 | 12/2019 | Kozlowski et al. |
| 2021/0330867 A1* | 10/2021 | Chang .................. A61K 31/337 |

\* cited by examiner

AMINO ACID-MODIFIED POLYMER FOR ADHESION PREVENTION AND APPLICATION THEREOF

CROSS-REFERENCE TO RELATED APPLICATIONS

This application claims the benefit of priority to U.S. Provisional Patent Application No. 63/014,756, filed Apr. 24, 2020, the entirety of which is incorporated by reference herein.

FIELD OF THE INVENTION

The present invention relates to amino acid-modified polymers and methods of making the same and using the same. The amino acid-modified polymers are thermosensitive and are capable of forming an absorbable mechanical barrier to reduce or to prevent post-operative tissue adhesions. Additionally, the amino acid-modified polymers are able to serve as a vector to deliver pharmaceutically active agents.

BACKGROUND OF THE INVENTION

Tissue or organ adhesions are bands of scar tissues that abnormally connect to internal tissues or organ surfaces, and surgery trauma is generally known as the most common factor to cause tissue adhesions. Postoperative tissue adhesions may result in severe clinical complications such as chronic pain, ischemia, intestinal obstruction, organ dysfunction, and the like, which often require reoperation for adhesiolysis. The reoperation can be fatal due to introducing of a number of risk factors, such as inadequate anesthesia, excessive bleeding, and postoperative inflammation, etc. Therefore, in order to prevent the postoperative tissue adhesions, introducing a physical barrier between the damaged tissue and adjacent tissues to obstruct the formation of tissue adhesion has been widely accepted and clinically used.

Various types of nature or synthetic polymers have been extensively explored as physical tissue barriers for preventing tissue adhesions, including film/sheet, liquid, and gel types. Film/sheet-type tissue barrier can physically isolate damaged tissue from the adjacent tissues, hence preventing tissue adhesion. Seprafilm® (Genzyme), prepared by cross-linking carboxymethylcellulose with hyaluronic acid, and Interceed® (Johnson & Johnson Medical), prepared by oxidized polymer cellulose, are the commercialized film/sheet-type materials used for adhesion prevention. However, film/sheet-type adhesion inhibitors are difficult to handle in an emergency surgical condition. Furthermore, film/sheet-type tissue barrier is not suitable to use when the application site is geographically complicated, microscopic, tubular-shaped, or is in any hard-to-reach area. Another drawback for the use of film/sheet adhesion inhibitors is that they may result in additional damages to the damage site during the suturing process.

Several liquid-type adhesion barriers, for example: Hyson®, prepared by 32% dextran solution and Adept®, prepared by 4% icodextrin solution, have been commercially used. Liquid-type adhesion inhibitors are easily to apply as an instillation to wash the entire wound after surgery. However, these materials commonly share one shortcoming in insufficient adherence to the application site. Therefore, they do not present sufficient antiadhesion efficacy.

In order to solve the aforementioned problems, a variety of gel-type adhesion barriers based on different polymer materials have been developed. Adcon-L (Gliatech), based on polylactic acid, Intergel® (Lifecore Biomedical), based on hyaluronic acid, Adba (Amitie), based on natural polymers, Spraygel (Confluent Surgical), based on polyethylene glycol, and Flowgel (Mediventures), based on polyethylene oxide-polypropylene oxide copolymers, etc., have been developed as gel-type adhesion inhibitors. Among all the gel-type antiadhesion materials, thermosensitive hydrogels are of particular interest because their pre-gel solutions can be directly administrated to the damage tissue by polymer solution coating, injecting, or spraying, and subsequently forming hydrogel in situ through temperature trigger. Furthermore, thermosensitive hydrogels also possess the ability to encapsulate pharmaceutically active agents such as anti-inflammatory drugs.

In comparison, gel-type antiadhesion materials are able to form a relatively stable barrier than the liquid-type adhesion inhibitors, and can greatly reduce the operation time as compared with the film/sheet-type adhesion inhibitors. However, gel-type antiadhesion materials usually suffer from early absorption due to rapid dissolution by the body before wounds heal, the early absorption eventually results in low adhesion-preventing efficacy.

U.S. Pat. No. 4,141,973 B1 discloses a composition where hyaluronic acid is used as a main compound for the purpose of preventing tissue adhesion. However, hyaluronic acid can be rapidly degraded in a living body with a short half-life in 3 days, indicating that hyaluronic acid is a material lacking sufficient retention time to prevent tissue adhesion. This disadvantage greatly limits single hyaluronic acid to function as a tissue adhesion inhibitor.

Pluronic or Poloxamer, a triblock copolymer that generally has a structure of A-poly(ethylene oxide)-B-poly(propylene oxide)-A-poly(ethylene oxide) (PEO-PPO-PEO), is a typical thermosensitive material that exhibits a thermos-reversible sol-gel transition behavior, and has been widely studied as an antiadhesion material. Generally, Pluronic is presence in a solution state at a low temperature, but gelation occurs after increasing temperature to a certain degree (U.S. Pat. Nos. 4,188,373, 4,474,751, 4,478,822). Such a sol-gel transition behavior can be influenced by factors including composition, concentration, molecular weight, environmental ion strength, pH value, additives, etc. Therefore, Pluronic-based polymers are highly attractive due to their versatile physicochemical and biocompatible properties. Although Pluronics exhibit excellent sol-gel phase transition behavior, their hydrous structures have many drawbacks when used as adhesion barriers, such as low mechanical strength, poor tissue adhesive ability, and rapid water-erosion property. Therefore, Pluronics suffer from short of residence time and thus cannot perform time-sufficient adhesion inhibition in the surgical site. In addition, Pluronics have also been widely studied as a vector in the areas of pharmaceutical science for decades, but their insufficient mechanical strength and poor water stability limit them inappropriate for vector applications. Although many attempts have been made to improve the antiadhesion and drug delivery abilities of Pluronic-based materials in recent years, none of ideal Pluronic-based antiadhesive and drug delivery materials has yet been made.

U.S. Pat. No. 9,327,049 B2 discloses a composition where Pluronics are used as main component for the purpose of preventing adhesion. In addition, the composition also has antibacterial and hemostatic properties. The composition comprises Poloxamer 188 (Pluronic® F-68), Poloxamer 407

(Pluronic® F-127), chitosan, and gelatin. Although chitosan has antibacterial and hemostatic activities, and has longer degradation time in a living body, the use of chitosan as a component in an antiadhesion barrier can be dangerous to patients allergic to chitin, so they are not suitable for those cases.

U.S. Pat. No. 9,895,446 B2 discloses a composition for intralesional delivery of chemotherapeutic agents. The composition comprises at least one anticancer drug and one or more Poloxamer compounds including Poloxamer 188 ($^{Pluronic}$® F-68), Poloxamer 407 (Pluronic® F-127) and the mixture of Poloxamers 188 and 407. However, despite the single use of Poloxamer 407 or 188 or to use the mixture of these two kinds of Poloxamers as a drug vector, the mechanical strengths of these materials are not strong enough to resist water-erosion, limiting their applications for sustainable drug release systems.

Despite current developments based on Pluronic materials in the field, additional improvements are still needed. Pluronics, as thermosensitive materials, have great potential to be ideal antiadhesion inhibitors and drug carriers if some of their structure defects could be addressed to enhance their mechanical strength, tissue adhesive ability, and water-resistant property. Although an ideal antiadhesion material or drug vector based on Pluronic has not yet been developed, at least a better antiadhesion ability and drug lease profile based on these materials will be achieved by the inventions disclosed hereinafter.

SUMMARY OF THE INVENTION

The first aspect of the present invention is to provide an amino acid-modified polymer having a structure of the following formula (I):

wherein:

POLY is a triblock copolymer of poly(ethylene oxide) (PEO)-poly(propylene oxide)(PPO)-poly(ethylene oxide) (PEO);

m and n are independently from each other 0 or 1, wherein m and n cannot be 0 simultaneously; and AA is an amino acid residue, where its amino group directly binds to the chain-end of the POLY to form carbamate (O—C(=O)—NH) linkage.

In one embodiment of the invention, the triblock copolymer of poly(ethylene oxide)(PEO)-poly(propylene oxide) (PPO)-poly(ethylene oxide)(PEO) is selected from Pluronic F-127 (PF127), Pluronic F-68 (PF68), and Pluronic L-35 (PL35).

In one or more embodiments, the amino acid residue is selected from hydrophobic amino acids, basic amino acids, acidic amino acids, aromatic amino acids, and hydrophilic amino acids.

In particular embodiments, the amino acid residue may be one of Leucine, Methionine, Lysine, Aspartic acid, Asparagine, Tyrosine, Serine, and Cysteine.

The second aspect of this invention is to provide a composition comprising any one of polymer having a structure of the following formula (I):

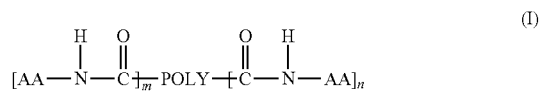

or combinations thereof,
wherein:

POLY is a triblock copolymer of poly(ethylene oxide) (PEO)-poly(propylene oxide)(PPO)-poly(ethylene oxide) (PEO);

m and n are independently from each other 0 or 1, wherein m and n cannot be 0 simultaneously; and AA is an amino acid residue, where its amino group directly binds to the chain-end of the POLY to form carbamate (O—C(=O)—NH) linkage.

In one embodiment of the invention, the triblock copolymer of poly(ethylene oxide)(PEO)-poly(propylene oxide) (PPO)-poly(ethylene oxide)(PEO) is selected from Pluronic F-127 (PF127), Pluronic F-68 (PF68), and Pluronic L-35 (PL35).

In one or more embodiments, the amino acid residue is selected from hydrophobic amino acids, basic amino acids, acidic amino acids, aromatic amino acids, and hydrophilic amino acids.

In particular embodiments, the amino acid residue may be one of Leucine, Methionine, Lysine, Aspartic acid, Asparagine, Tyrosine, Serine, and Cysteine.

The third aspect of this invention is to provide a use of the polymer and the composition for the prevention of postoperative tissue adhesion and for drug delivery.

In one or more embodiments, the invention features an amino acid-modified polymer with improved loading capacity and better release profile for delivery of pharmaceutically active agents.

The pharmaceutically active agent is selected from the group consisting of anticancer drugs, antibiotics, steroids, hemostatic agents, non-steroidal anti-inflammatory drugs, hormones, analgesics, and anesthetics. Preferably, Paclitaxel.

Obviously, based on the above description of the invention, other various modifications, substitutions, or alterations can be made without departing from the basic technical idea of the invention, with reference to common technical knowledge and conventional means in the art.

BRIEF DESCRIPTION OF THE DRAWINGS

A more complete understanding of the subject matter can be derived by referring to the detailed description and claims when considered in conjunction with the following figures. Each of the following figures is provided for illustration of the performed embodiments only, and the scope of the present invention is not to be restricted by these figures thereto.

Figure 2:
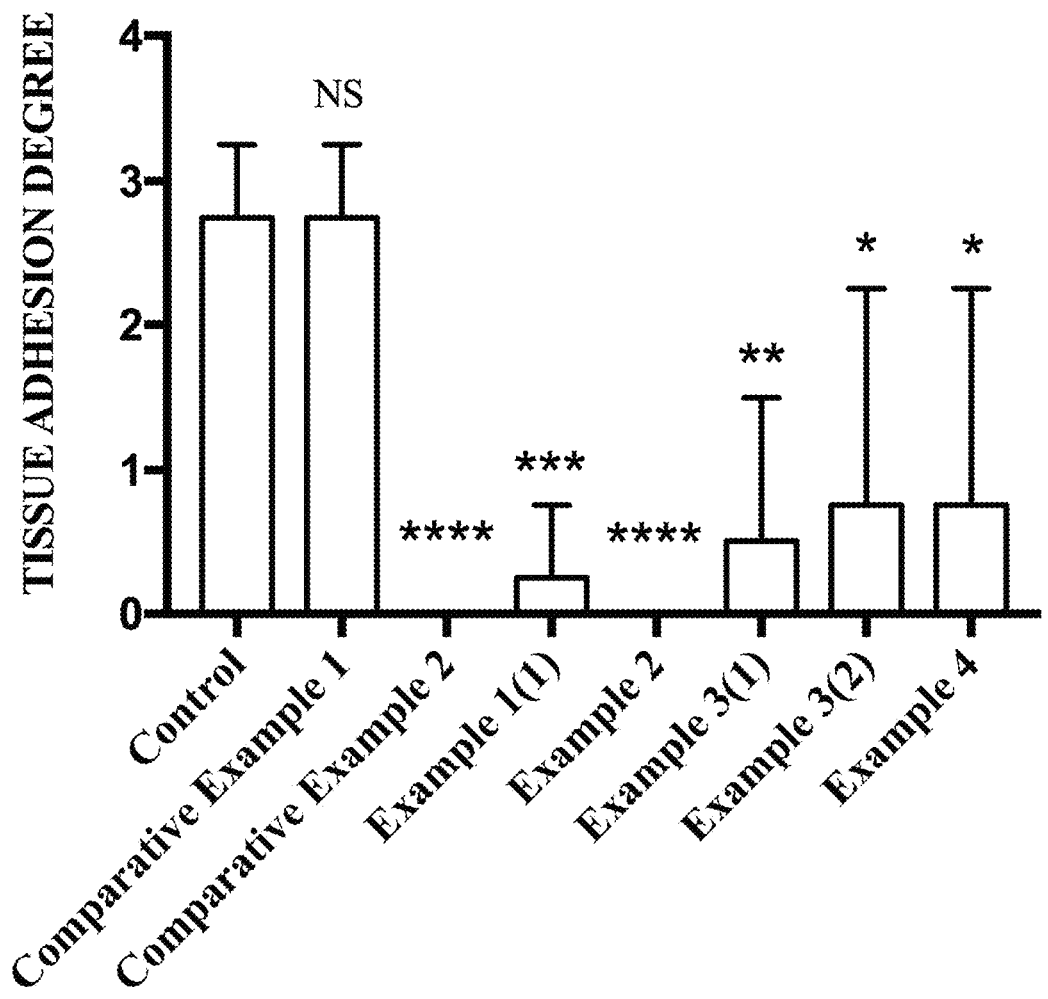

FIG. 2 illustrates the results of evaluating tissue adhesions using the Hoffmann adhesion scoring system. The statistical differences between the control and experimental groups were analyzed by the Student's t-test with two-tailed calculation using Prism 7 for Mac (GraphPad Software, USA). A value of p<0.05 was considered statistical significance, and * indicates p<0.05,  indicates p<0.01, * indicates p<0.001, **** indicates p<0.0001, and NS represents not significant difference.

Figure 3A:
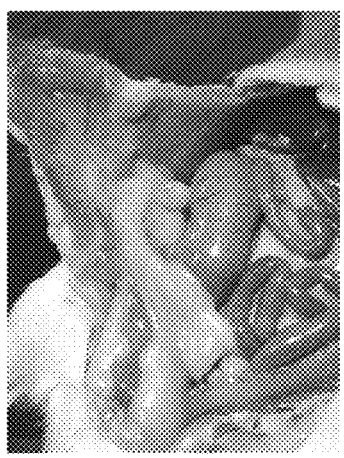

FIG. 3A illustrates the tissue adhesion of the control group.

Figure 3B:

FIG. 3B illustrates the tissue adhesion after treatment of Comparative Example 1.

Figure 3C:
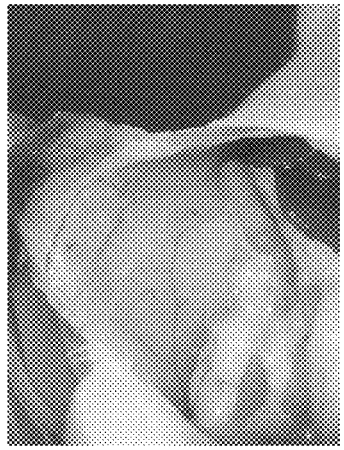

FIG. 3C illustrates the tissue adhesion after treatment of Example 1(1).

Figure 3D:

FIG. 3D illustrates the tissue adhesion after treatment of Example 2.

Figure 3E:
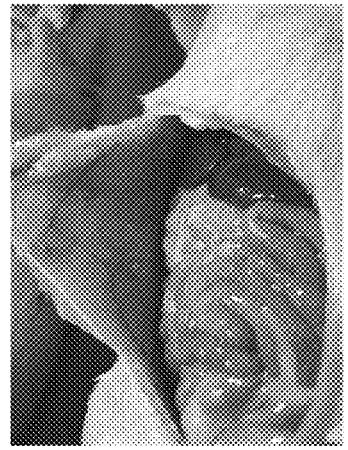

FIG. 3E illustrates the tissue adhesion after treatment of Comparative Example 2.

Figure 4A:
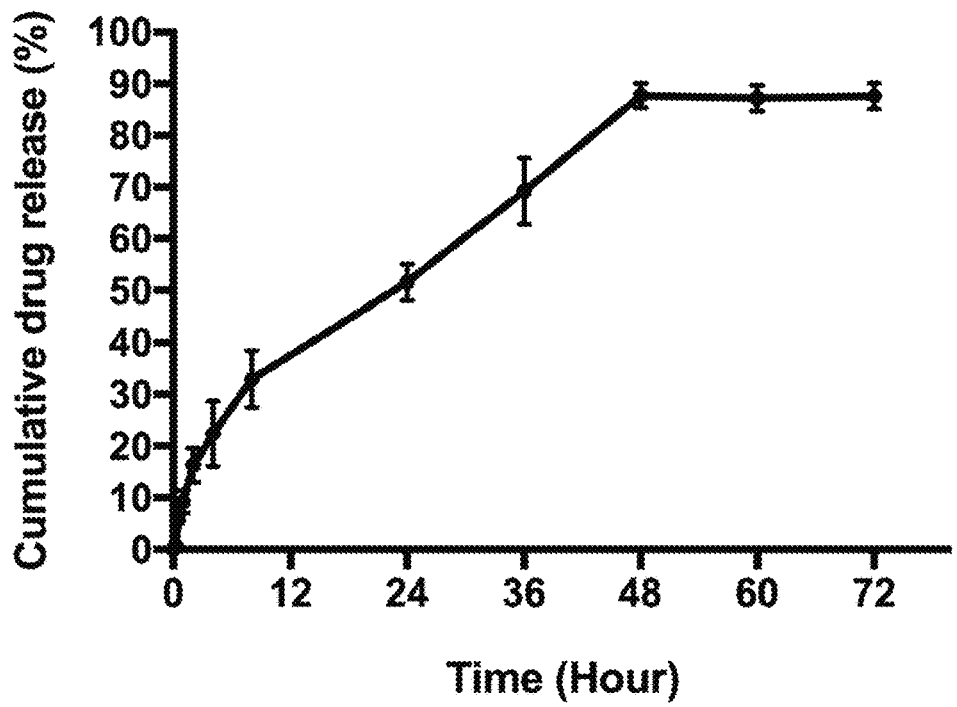

FIG. 4A illustrates the PTX release profile of the hydrogel prepared from Comparative Example 1.

Figure 4B:
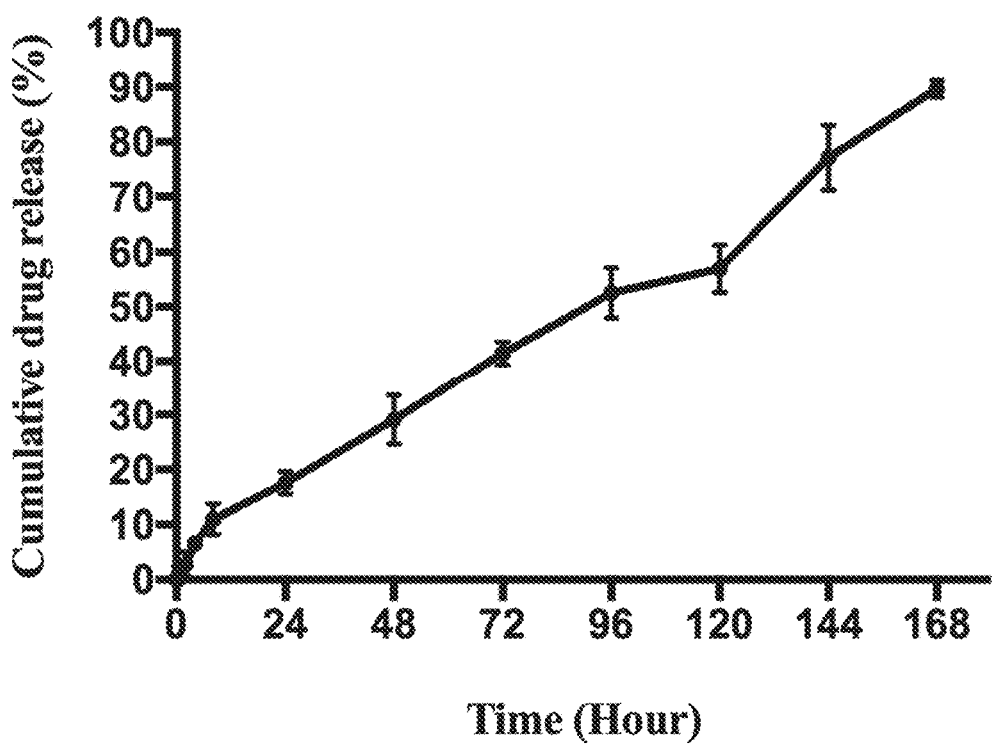

FIG. 4B illustrates the PTX release profile of the hydrogel prepared from Example 2.

Figure 4C:
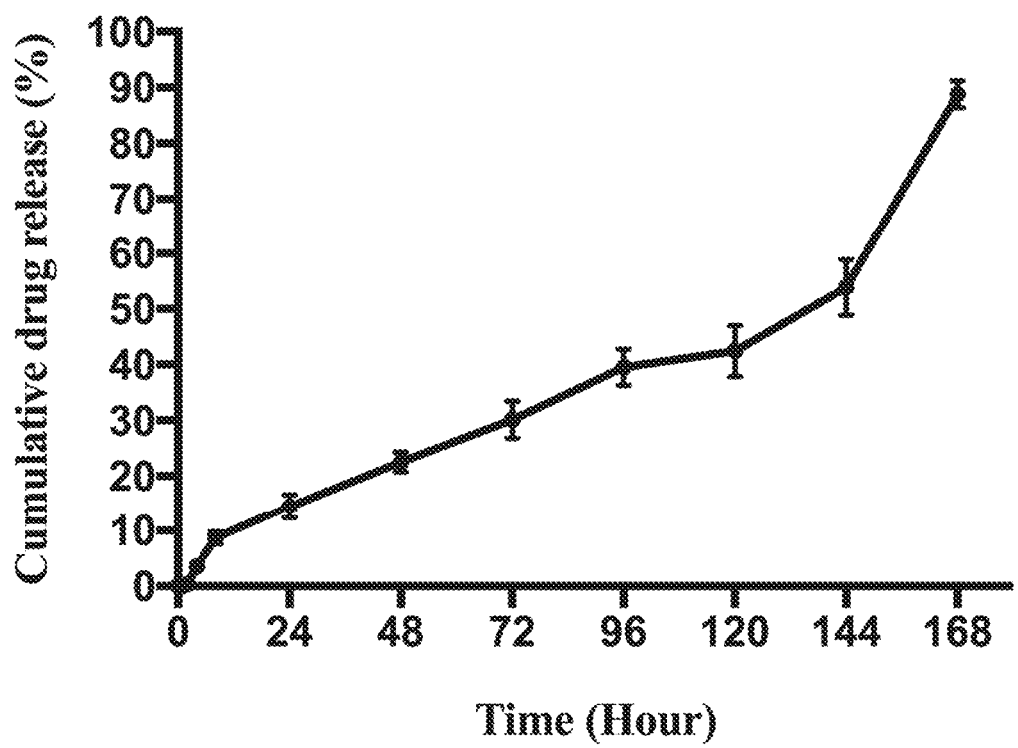

FIG. 4C illustrates the PTX release profile of the hydrogel prepared from Example 5(2).

DETAILED DESCRIPTION OF THE INVENTION

Before detailed describing one or more embodiments of the present invention, it is important to be noted that, as used in this specification and the claims, the singular forms "a.", "an." and "the" include plural referents unless the context clearly specified otherwise. Therefore, for example, reference to "an amino acid" includes a single amino acid as well as two or more of the same or different amino acids, reference to "chain-end of polymer" includes a single chain-end as well as two or more of the same or different chain-end of polymers, and the like.

In describing and claiming the present invention, unless otherwise specified, the terms used herein have the following definitions:

As used herein, the terms "comprises," "comprising," "includes," "including," "has," "having" or any other variation thereof are intended to cover a non-exclusive inclusion. For example, a component, structure, article, or apparatus that comprises a list of elements is not necessarily limited to only those elements but may include other elements not expressly listed or inherent to such component, structure, article, or apparatus.

The term "Amino acids" refers to the structural units of proteins. The twenty amino acids encoded by the genetic code are called "standard amino acids." These amino acids have the structure H2N—CHR—COOH, where R is a side chain specific to the amino acids. Standard amino acids are Alanine, Arginine, Aspargine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, and Valine. Amino acids can be classified into five groups, specifically, hydrophobic amino acids, hydrophilic amino acids, basic amino acids, acidic amino acids, and aromatic amino acids. As used herein, amino acids can be present in two stereoisometric forms, called "D." and "L." described herein.

The amino acid-modified polymer and composition of the present invention can be administered to prevent adhesions in the context of any of a variety of postoperative types. As used herein, the term "postoperative" refers to examples of postoperative procedures in which the amino acid-modified polymer and composition of the invention are of use include, without limitation, abdominal, abdominopelvic, ophthalmic, orthopedic, gastrointestinal, thoracic, cranial, head and neck, cardiovascular, gynecological, obstetric, joint (e.g., arthroscopic), urologic, plastic, reconstructive, musculoskeletal, and neuromuscular surgeries.

According to the present invention, it is possible to effectively prevent postoperative tissues adhesion. The antiadhesive polymer and composition thereof used in the present invention may have any form such as powder, solution or gel form, and therefore, for example, is easy to perform even in relatively localized surgery such as endoscopic surgery.

The antiadhesive polymer and composition thereof used in the present invention can be applied on the surgery by, for example, coating or spraying onto a wound site and the surfaces of organs located around the wound site or surrounding tissues. The application may be performed at one time or with a plurality of times coating or spraying onto a local portion of the surface of the target organ or surrounding tissues. Also, a coating or spraying device may be used. The device can be a prefilled syringe. The dose can be appropriately selected or adjusted by a person skilled in the art.

The term "amino acid-modified polymer" refers to a polymer with its chain-end bound with an amino acid and/or a polyamino acid through a carbamate linkage, wherein the polymer may be a block copolymer, and may contain two or more blocks. Further, the copolymer may be a Pluronic that is a triblock polymer, consisting of poly(ethylene oxide)(PEO)-poly(propylene oxide)(PPO)-poly(ethylene oxide)(PEO). The structure of the amino acid-modified polymer is represented by the following Formula (I):

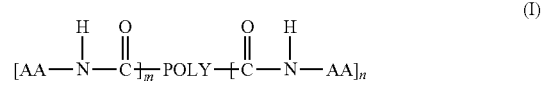

wherein:

POLY represents a copolymer comprising poly(ethylene oxide)(PEO)-poly(propylene oxide)(PPO)-poly(ethylene oxide)(PEO), m and n are independently from each other 0 or 1, wherein m and n cannot be 0 simultaneously, and AA represents an amino acid or a polyamino acid residue, where its amino group directly binds to a chain-end of the POLY to form a carbamate bond, wherein AA is selected from the groups consisting of hydrophobic amino acids, basic amino acids, acidic amino acid, aromatic amino acids, and hydrophilic amino acids. Wherein, the hydrophobic amino acids comprising hydrophobic amino acids and/or hydrophobic polyamino acids, for example, Glycine, Alanine, Valine, Methionine, Leucine, Isoleucine, Phenylalanine and polymers thereof; the basic amino acids comprising basic amino acids and/or basic polyamino acids, for example, Lysine, Histidine, Arginine and polymers thereof; the acidic amino acids comprising acidic amino acids and/or acidic polyamino acids, for example, Aspartic acid, Asparagine, glutamic acid and polymers thereof; the aromatic amino acids comprising aromatic amino acids and/or aromatic polyamino acids, for example, Tyrosine, Tryptophan and polymers thereof; and the hydrophilic amino acids comprising hydrophilic amino acids and/or hydrophilic polyamino acids, for example, Serine, Threonine, Cysteine, Proline and polymers thereof.

The term "amino acid-modified polymer composition" refers to a composition comprising any one of polymer having a structure of Formula (I), or combinations thereof, wherein:

POLY represents a copolymer comprising poly(ethylene oxide)(PEO)-poly(propylene oxide)(PPO)-poly(ethylene oxide)(PEO), m and n are independently from each other 0 or 1, wherein m and n cannot be 0 simultaneously, and AA represents an amino acid or a polyamino acid residue, where its amino group directly binds to a chain-end of the POLY to form a carbamate bond, wherein AA is selected from the groups consisting of hydrophobic amino acids, basic amino acids, acidic amino acid, aromatic amino acids, and hydrophilic amino acids. Wherein, the hydrophobic amino acids comprising hydrophobic amino acids and/or hydrophobic polyamino acids, for example, Glycine, alanine, Valine, Methionine, Leucine, Isoleucine, Phenylalanine and polymers thereof; the basic amino acids comprising basic amino acids and/or basic polyamino acids, for example, Lysine, Histidine, Arginine and polymers thereof; the acidic amino acids comprising acidic amino acids and/or acidic polyamino acids, for example, Aspartic acid, Asparagine, Glutamic acid and polymers thereof; the aromatic amino acids comprising aromatic amino acids and/or aromatic polyamino acids, for example, Tyrosine, Tryptophan and polymers thereof; and the hydrophilic amino acids comprising hydrophilic amino acids and/or hydrophilic polyamino acids, for example, Serine, Threonine, Cysteine, Proline and polymers thereof.

The term "in an amount of" refers to the weight of any one of the polymer or combinations thereof based on the composition in the present invention. The polymer or combinations thereof may be used in an amount selected from a range of 5% to 30% by weight, 7% to 25% by weight, preferably 10% to 20% by weight, 12% to 18% by weight, or more preferably 13% to17% by weight based on a total weight of the composition.

The term "polymer combination" refers to a combination that is mixed two or more of the different amino acid-modified polymers. Herein, a combination of two amino acid-modified polymers, each polymer of the combination may be included in a weight ratio of 99:1 to 1:99, 90:10 to 10:90, 80:20 to 20:80, 70:30 to 30:70, 60:40 to 40:60, or 90:10 to 50:50, and, for example, may be included in a weight ratio of 95:5 to 30:70, 80:20 to 40:60 or 70:30 to 50:50.

The term "chemically activated copolymer solution" refers to a copolymer comprising poly(ethylene oxide) (PEO)-poly(propylene oxide)(PPO)-poly(ethylene oxide) (PEO) which is dissolved into a solvent comprising a catalyst that creates active carbonate esters at the chain-ends of the copolymer where allowing further reaction with amino acids to form a polymeric amino acid derivative.

The term "biocompatible" refers to a material that is substantially non-toxic, non-immunogenic and non-irritant to recipients' cells in the quantities and at the location used, and also does not elicit or cause a significant deleterious or undesirable effect on the recipient's body at the location used.

The term "adhesion prevention" refers to administering a composition for prevention of adjacent tissues or organ surfaces from adhering together so as to cause a reduction in the number of adhesions, extent of adhesions (e.g., area), and/or severity of adhesions (e.g., thickness or resistance to mechanical or chemical disruption) relative to the number, extent, and/or severity of adhesions that would occur without such administration.

The term "adhesion inhibitor" refers to administering or applying a composition for inhibiting adjacent tissues or surface of organs adhering together.

The term "vector" refers to a carrier that is capable of carrying and releasing pharmaceutically active agents.

The term "vector applications" refers to applications which require a carrier to deliver and release pharmaceutically active agents.

The term "carbamate linkage" refers to a carbamate binding between an amino group of an amino acid and a carbonate ester at the chain-end of a polymer. The chemical structure of such carbamate linkage is represented as the following Formula (II):

(II)

The term "pharmaceutically active agent" refers to any medicinal useful substance which may have certain therapeutic, preventive and/or diagnostic effects to a human or animal body. Herein, the pharmaceutically active agent is selected from the group consisting of anticancer drugs, antibiotics, hemostatic agents, steroids, non-steroidal anti-inflammatory drugs, hormones, analgesics, and anesthetics. Preferably, the anticancer drugs is Paclitaxel.

The term "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient.

In this invention, the amino acid-modified polymer and polymer composition may presence as a hydrogel, and may be temperature-sensitive. Therefore, the polymer and polymer composition may allow a reversible transitioning between sol and gel states upon change of temperature, and the temperature of the sol-gel phase transition (gelation) may be controlled by adjusting the contents of the polymer. The polymer and/or polymer composition may present a sol state at room temperature, but transform into a gel state when temperature is below human body temperature, herein between 28° C. to 34° C., and thus they may be injected or sprayed into a surgical site in a human or animal body, providing sufficient wound coverage. After being applied into the surgical site, the polymer and/or polymer composition may subsequently undergo a gelation and adhere to the wound as a barrier to prevent tissue adhesion.

The amino acid-modified polymer and polymer composition may allow a thermosensitive sol-gel state transitioning which enables them to act as a vector to perform transdermal, injectable, sprayable and controlled delivery of many pharmaceutically active agents.

Pluronic, a copolymer comprising poly(ethylene oxide) (PEO)-poly(propylene oxide)(PPO)-poly(ethylene oxide) (PEO), has been reported exhibiting a thermo-reversible sol-gel phase transition behavior and a certain anti-adhesion ability, which is widely studied for both adhesion prevention and vector application. However, it has low anti-adhesion efficiency and poor drug release profile in a human body caused by poor mechanical strength, weak tissue adhesiveness, and rapid water dissolution (less than 2 days).

In this invention, pure Pluronic, which serves an unmodified comparative example of our compounds, is used as a comparison to evaluate the improvement on the adhesion prevention efficacy contributed from the amino acid-modified polymer. Accordingly, as a result of extensive research, the inventors of this application have found that Pluronic with modification by some amino acids may: (1) enhance the mechanical strength of the polymer structure, (2) improve the fluidity of the polymer, giving it more usability in biomedical applications, (3) increase the water-erosion resistance ability, (4) increase the adhesiveness between the polymer and tissues, (5) enhance the tissue adhesion prevention ability, (6) increase loading capacity in delivery of pharmaceutically active agents, and (7) improve the release profile in delivery of pharmaceutically active agents.

available from Acrose. N, N'-disuccinimidyl carbonate (hereinafter referred to as "DSC") and Paclitaxel (hereinafter referred to as "PTX") were available from Fluorochem. L-Aspartic acid, L-Asparagine, L-Lysine, L-Serine, and L-Tyrosine were available from Acrose. L-Leucine, L-Cysteine, and L-Methionine were available from cj haide (ningbo) biotech co. ltd.

EXAMPLE 1

Preparation of Hydrophobic Amino Acid-Modified Pluronic (1) Leucine-Modified Pluronic F-127

A hydrophobic amino acid, L-Leucine, in an amount of 4.8 mmole was dissolved in an alkaline solution to form an

REACTION SCHEME

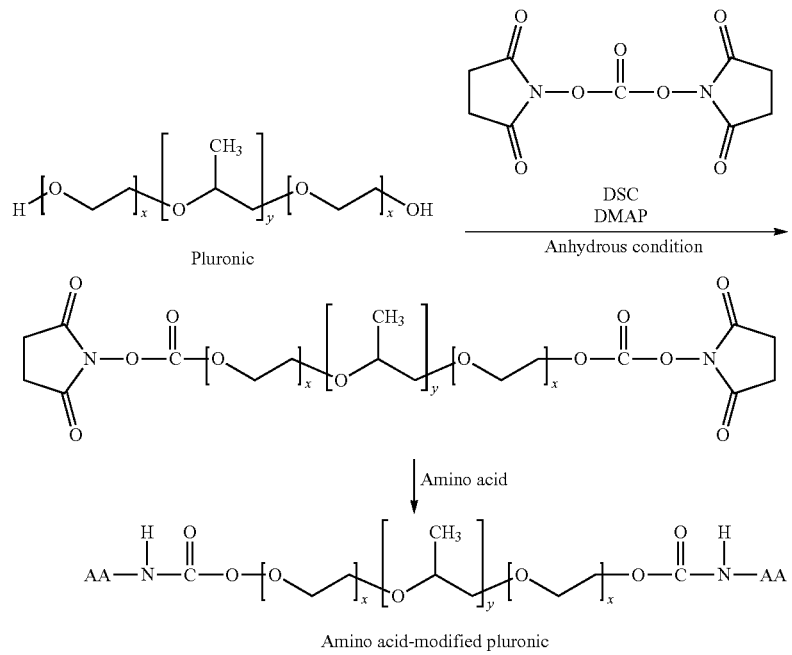

Experimental

The present invention is performed using conventional technique of organic synthesis, biochemistry, rheology, and the like, which are known to those skilled in the art.

Hereinafter, the present invention will be described in more detail with reference to examples. However, each of the following examples is provided for illustration of the performed embodiments only, and the scope of the present invention is not to be restricted by these examples thereto.

Materials

The chemicals used to perform the Examples and Comparative Examples are as follows:

Pluronic-F127 (12,500 Da), Pluronic F-68 (8,400 Da), and Pluronic L-35 (1,900 Da) were available from BASF Corporation. Anhydrous tetrahydrofuran (hereinafter referred to as "THF"), 4-dimethylaminopyridine (hereinafter referred to as "DMAP"), and anhydrous dimethyl sulfoxide (hereinafter referred to as "anhydrous DMSO") were amino acid solution. Pluronic F-127 in an amount of 0.6 mmole and 4.8 mmole of DMAP were dissolved in 30 mL of anhydrous THF to obtain a clear solution. After 30 minutes stirring, 10 mL of anhydrous DMSO containing 4.8 mmole of DSC were dropwise added within 1 hour, and the mixture was stirred at room temperature for 24 hours. Process was all carried out under nitrogen atmosphere. After 24 hours, the Leucine-contained solution was added and the mixture was kept stirring for 24 hours. The resulting Leucine-modified Pluronic solution was purified by dialysis, and was dried by lyophilization to yield white polymer powders (yield: 45%). $^1$H NMR (600 MHz, $D_2O$): δ 4.30, 4.21 (m, —$CH_2$—O—(C═O)—NH—), 4.01 (m, —O—(C═O)—NH—CH—), 1.70 (m, —$CH_2$—CH—$(CH_3)_2$), 1.60 (m, —CH—$(CH_3)_2$), 0.96 (m, —CH—$(CH_3)_2$); FTIR: 780 $cm^{-1}$ (—NH wag), 1531 $cm^{-1}$ (—CNH), 1569 $cm^{-1}$ (—(C═O)—NH—), 1731 $cm^{-1}$ (—(C═O)).

The exemplary chemical structure of the Leucine-modified Pluronic F-127 is provided as following:

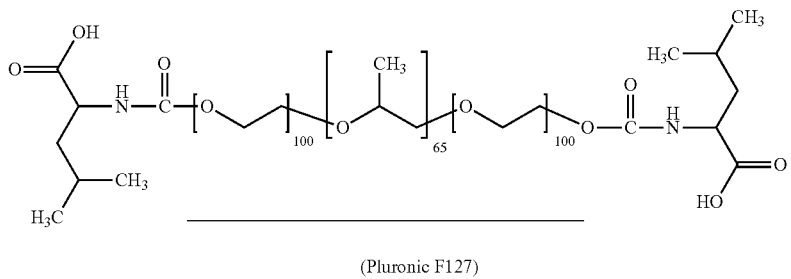

(Pluronic F127)

(2) Leucine-Modified Pluronic F-68

A hydrophobic amino acid, L-Leucine, in an amount of 4.8 mmole was dissolved in an alkaline solution to form an amino acid solution. Pluronic F-68 in an amount of 0.6 mmole and 4.8 mmole of DMAP were dissolved in 30 mL of anhydrous THF to obtain a clear solution. After 30 minutes stirring, 10 mL of anhydrous DMSO containing 4.8 mmole of DSC were dropwise added within 1 hour, and the mixture was stirred at room temperature for 24 hours. Process was all carried out under nitrogen atmosphere. After 24 hours, the Leucine-contained solution was added and the mixture was kept stirring for 24 hours. The resulting Leucine-modified Pluronic solution was purified by dialysis, and was dried by lyophilization to yield white polymer powders (yield: 40%). $^1$H NMR (600 MHz, $D_2O$): δ 4.28, 4.23 (m, —$CH_2$—O—(C=O)—NH—), 4.06 (m, —O—(C=O)—NH—CH—), 1.72 (m, —$CH_2$—CH—$(CH_3)_2$), 1.62 (m, —CH—$(CH_3)_2$), 0.97 (m, —CH—$(CH_3)_2$); FTIR: 780 $cm^{-1}$ (—NH wag), 1531 $cm^{-1}$ (—CNH), 1569 $cm^{-1}$ (—(C=O)—NH—), 1731 $cm^{-1}$ (—(C=O)).

The exemplary chemical structure of the Leucine-modified Pluronic F-68 is provided as following:

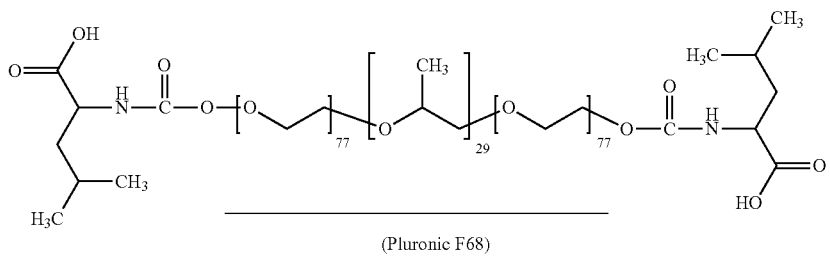

(Pluronic F68)

(3) Leucine-Modified Pluronic L-35

A hydrophobic amino acid, L-Leucine, in an amount of 4.8 mmole was dissolved in an alkaline solution to form an amino acid solution. Pluronic L-35 in an amount of 0.6 mmole and 4.8 mmole of DMAP were dissolved in 30 mL of anhydrous THF to obtain a clear solution. After 30 minutes stirring, 10 mL of anhydrous DMSO containing 4.8 mmole of DSC were dropwise added within 1 hour, and the mixture was stirred at room temperature for 24 hours. Process was all carried out under nitrogen atmosphere. After 24 hours, the Leucine-contained solution was added and the mixture was kept stirring for 24 hours. The resulting Leucine-modified Pluronic solution was purified by dialysis, and was dried by lyophilization to yield white polymer powders (yield: 35%). $^1$H NMR (600 MHz, $D_2O$): δ 4.30 (m, —O—(C=O)—NH—CH—), 4.22 (m, —$CH_2$—O—(C=O)—NH—), 1.70 (m, —$CH_2$—CH—$(CH_3)_2$), 1.61 (m, —CH—$(CH_3)_2$), 0.97 (m, —CH—$(CH_3)_2$); FTIR: 780 $cm^{-1}$ (—NH wag), 1531 $cm^{-1}$ (—CNH), 1569 $cm^{-1}$ (—(C=O)—NH—), 1731 $cm^{-1}$ (—(C=O)).

The exemplary chemical structure of the Leucine-modified Pluronic L-35 is provided as following:

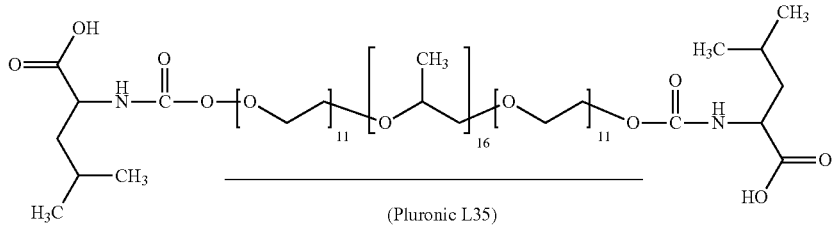

(Pluronic L35)

(4) Methionine-Modified Pluronic F-127

A hydrophobic amino acid, L-Methionine, in an amount of 4.8 mmole was dissolved in an alkaline solution to form an amino acid solution. Pluronic F-127 in an amount of 0.6 mmole and 4.8 mmole of DMAP were dissolved in 30 mL of anhydrous THF to obtain a clear solution. After 30 minutes stirring, 10 mL of anhydrous DMSO containing 4.8 mmole of DSC were dropwise added within 1 hour, with continued stirring at room temperature for 24 hours. Process was all carried out under nitrogen atmosphere. After 24 hours, the solution containing Methionine was added and the mixture was stirred for 24 hours. The resulting Methionine-modified Pluronic solution was purified by dialysis, and was dried by lyophilization to yield white polymer powders (yield: 45%). $^1$H NMR (600 MHz, D$_2$O): δ 4.30 (m, —O—(C=O)—NH—CH—), 4.23 (m, —CH$_2$—O—(C=O)—NH—), 2.61 (m, —CH$_2$—CH$_2$—S—CH$_3$), 2.16 (s, —S—CH$_3$), 2.13, 1.96 (m, —CH$_2$—CH$_2$—S—CH$_3$); FTIR: 1215 cm$^{-1}$ (—CNH), 1603 cm$^{-1}$ (—(C=O)—NH—), 1733 cm$^{-1}$ (—(C=O)).

EXAMPLE 2

Preparation of Basic Amino Acid-Modified Pluronic Lysine-Modified Pluronic F-127

A basic amino acid, L-Lysine, in an amount of 2.4 mmole was dissolved in distilled water to form an amino acid solution. Pluronic F-127 in an amount of 0.6 mmole and 4.8 mmole of DMAP were dissolved in 30 mL of anhydrous THF to obtain a clear solution. After 30 minutes stirring, 10 mL of anhydrous DMSO containing 4.8 mmole of DSC were dropwise added within 1 hour, the mixture was stirred at room temperature for 24 hours. Process was all carried out under nitrogen atmosphere. After 24 hours, the Lysine-contained solution was added and the mixture was kept stirring for 24 hours. The resulting Lysine-modified Pluronic solution was purified by dialysis, and was dried by lyophilization to yield white polymer powders (yield: 45%). $^1$H NMR (600 MHz, D$_2$O): δ 4.25 (m, —CH$_2$—O—(C=O)—NH—), 3.16 (m, —O—(C=O)—NH—CH$_2$—), 1.81, 1.70 (m, NH—CH$_2$—CH$_2$—CH$_2$—CH$_2$), 1.57 (m, NH—CH$_2$—CH$_2$—CH$_2$—), 1.41 (m, NH—CH$_2$—CH$_2$—CH$_2$—CH$_2$—, 2H); FTIR: 776 cm$^{-1}$ (—NH wag), 1557 cm$^{-1}$ (—CNH), 1710 cm$^{-1}$ (—(C=O)).

EXAMPLE 3

Preparation of Acidic Amino Acid-Modified Pluronic (1) Aspartic Acid-Modified Pluronic F-127

An acidic amino acid, L-Aspartic acid, in an amount of 4.8 mmole was dissolved in an alkaline solution to form an amino acid solution. Pluronic F-127 in an amount of 0.6 mmole and 4.8 mmole of DMAP were dissolved in 30 mL of anhydrous THF to obtain a clear solution. After 30 minutes stirring, 10 mL of anhydrous DMSO containing 4.8 mmole of DSC were dropwise added within 1 hour, and the mixture was with continued stirring at room temperature for 24 hours. Process was all carried out under nitrogen atmosphere. After 24 hours, the solution containing Aspartic acid was added and the mixture was stirred for 24 hours. The resulting Aspartic acid-modified Pluronic solution was purified by dialysis, and was dried by lyophilization to yield white polymer powders (yield: 45%). $^1$H NMR (600 MHz, D$_2$O): δ 4.38 (m, —O—(C=O)—NH—CH—), 4.26 (m, —CH$_2$—O—(C=O)—NH—), 2.70, 2.51 (m, —CH$_2$—(C=O)—OH); FTIR: 776 cm$^{-1}$ (—NH wag), 1557 cm$^{-1}$ (—CNH), 1710 cm$^{-1}$ (—(C=O)).

(2) Asparagine-Modified Pluronic F-127

An acidic amino acid, L-Asparagine, in an amount of 2.4 mmole was dissolved in an alkaline solution to form an amino acid solution. Pluronic F-127 in an amount of 0.6 mmole and 4.8 mmole of DMAP were dissolved in 30 mL of anhydrous THF to obtain a clear solution. After 30 minutes stirring, 10 mL of anhydrous DMSO containing 4.8 mmole of DSC were dropwise added within 1 hour, and the mixture was kept stirring at room temperature for 24 hours. Process was all carried out under nitrogen atmosphere. After 24 hours, the solution containing Asparagine was added and the mixture was stirred for 24 hours. The resulting Aspartic acid-modified Pluronic solution was purified by dialysis, and was dried by lyophilization to yield white polymer powders (yield: 45%). $^1$H NMR (600 MHz, D$_2$O): δ 4.35 (m, —O—(C=O)—NH—CH—), 4.27 (m, —CH$_2$—O—(C=O)—NH—), 2.82, 2.68 (m, —CH$_2$—(C=O)—NH$_2$); FTIR: 1416 cm$^{-1}$ (—CN), 1680 cm$^{-1}$ (—(C=O)—NH—), 1720 cm$^{-1}$ (—(C=O)).

EXAMPLE 4

Preparation of Aromatic Amino Acid-Modified Pluronic Tyrosine-Modified Pluronic F-127

An aromatic amino acid, L-Tyrosine, in an amount of 4.8 mmole was dissolved in an alkaline solution to form an amino acid solution. Pluronic F-127 in an amount of 0.6 mmole and 4.8 mmole of DMAP were dissolved in 30 mL of anhydrous THF to obtain a clear solution. After 30 minutes stirring, 10 mL of anhydrous DMSO containing 4.8 mmole of DSC were dropwise added within 1 hour, and the mixture was kept stirring at room temperature for 24 hours. Process was all carried out under nitrogen atmosphere. After 24 hours, the solution with Tyrosine was added and the mixture was stirred for 24 hours. The resulting Tyrosine-modified Pluronic solution was purified by dialysis, and was dried by lyophilization to yield white polymer powders (yield: 40%). $^1$H NMR (600 MHz, D$_2$O): δ 7.20 (d, $^2$CH, $^6$CH -phenyl ring), .6.89 (d, $^3$CH, $^5$CH -phenyl ring), 4.21 (m, —CH$_2$—O—(C=O)—NH—), 4.11 (m, —O—(C=O)—NH—CH—), 3.15, 2.83 (m, —CH$_2$-ph); FTIR: 1403 cm$^{-1}$ (—CN), 1517 cm$^{-1}$ (—CNH), 1604 cm$^{-1}$ (—C—C—/C=C), 1710 cm$^{-1}$ (—(C=O)).

EXAMPLE 5

Preparation of Hydrophilic Amino Acid-Modified Pluronic (1) Serine-Modified Pluronic F-127

A hydrophilic amino acid, L-Serine, in an amount of 4.8 mmole was dissolved in distilled water to form an amino acid solution. Pluronic F-127 in an amount of 0.6 mmole and 4.8 mmole of DMAP were dissolved in 30 mL of anhydrous THF to obtain a clear solution. After 30 minutes stirring, 10 mL of anhydrous DMSO containing 4.8 mmole of DSC were dropwise added within 1 hour, and the mixture was continuous stirred at room temperature for 24 hours. Process was all carried out under nitrogen atmosphere. After 24 hours, the solution with Serine was added and the mixture was stirred for 24 hours. The resulting Serine-modified Pluronic solution was purified by dialysis, and was dried by lyophilization to yield white polymer powders (yield: 40%). $^1$H NMR (600 MHz, D$_2$O): δ 4.30 (m, —CH$_2$—O—(C=O)—NH—), 4.16 (m, —O—(C=O)—NH—CH—), 3.93, 3.83 (m, —CH$_2$—OH); FTIR: 1410 cm$^{-1}$ (—CN), 1604 cm$^{-1}$ (—(C=O)—NH—), 1720 cm$^{-1}$ (—(C=O)).

(2) Cysteine-Modified Pluronic F-127

A hydrophilic amino acid, L-Cysteine, in an amount of 4.8 mmole was dissolved in an alkaline solution to form an amino acid solution. Pluronic F-127 in an amount of 0.6 mmole and 4.8 mmole of DMAP were dissolved in 30 mL of anhydrous THF to obtain a clear solution. After 30 minutes stirring, 10 mL of anhydrous DMSO containing 4.8 mmole of DSC were dropwise added within 1 hour, and the mixture was with continued stirring at room temperature for 24 hours. Process was all carried out under nitrogen atmosphere. After 24 hours, the solution containing Cysteine was added and the mixture was kept stirring for 24 hours. The resulting Cysteine-modified Pluronic solution was purified by dialysis, and was dried by lyophilization to yield white polymer powders (yield: 50%). $^1$H NMR (600 MHz, D$_2$O): δ 4.46 (m, —O—(C=O)—NH—CH—), 4.27 (m, —CH$_2$—O—(C=O)—NH—), 3.20, 2.98 (m, —CH$_2$—SH); FTIR: 1412 cm$^{-1}$ (—CN), 1515 cm$^{-1}$ (—CNH), 1604 cm$^{-1}$ (—(C=O)—NH—), 1700 cm$^{-1}$ (—(C=O)).

EXPERIMENTAL EXAMPLE 1

Rheology Characterization of Amino-Acid Modified Polymer (1) Preparation of amino acid-modified polymer hydrogels Each of amino acid-modified Pluronic F-127 prepared from Examples 1-5 was dissolved in distilled water with a final concentration of 15% (w/v).

(2) Preparation of Comparative Example 1

An amount of Pluronic F127, was added with a quantity of distilled water to form a polymer hydrogel with a final concentration of 15% (w/v).

(3) Rheology Characterization

Figure 1A:
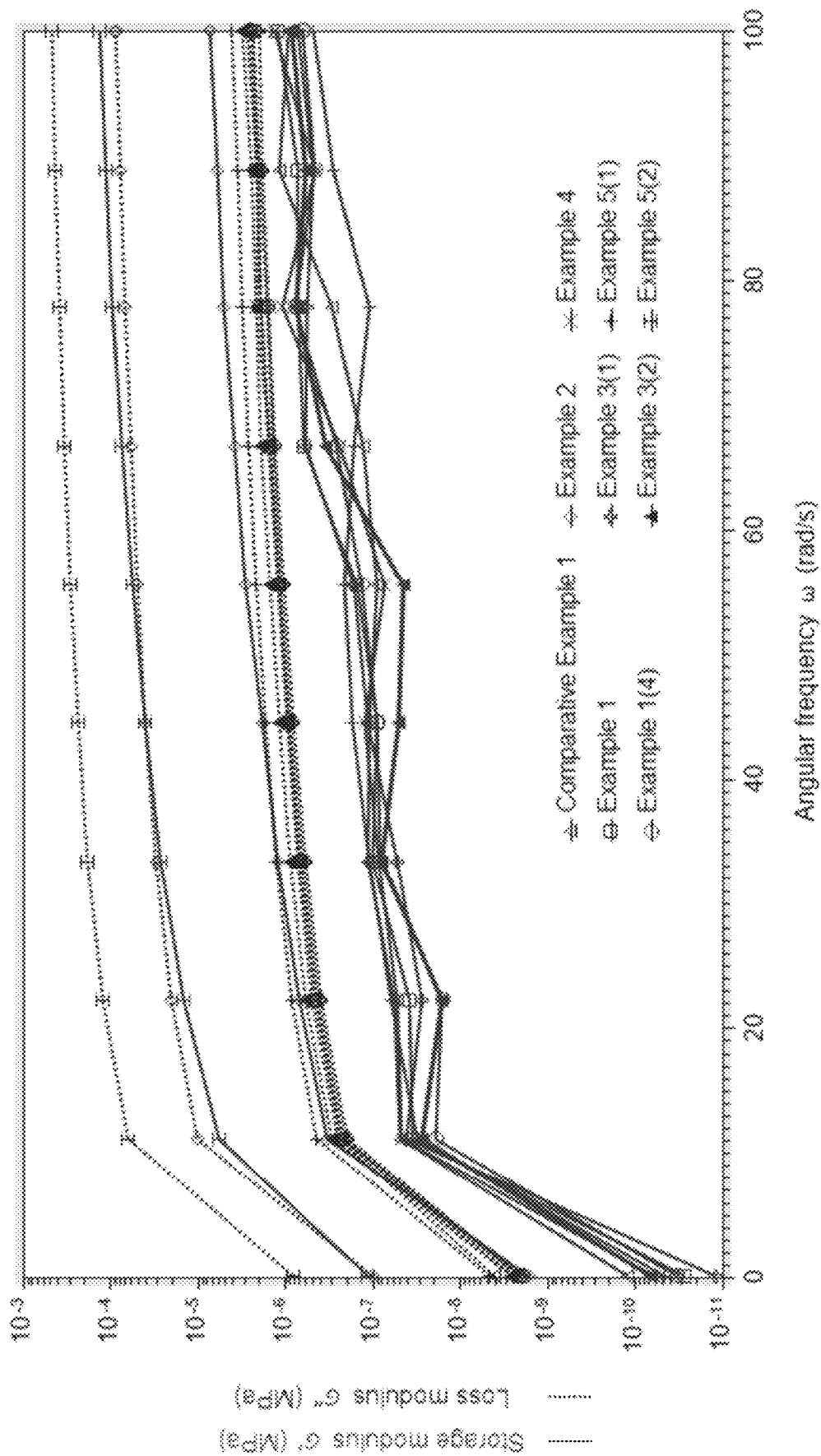
FIG. 1A illustrates the storage and loss modului of the amino acid-modified Pluronic prepared from Examples 1-5 and the unmodified Pluronic prepared in Comparative Example 1. The measurement was performed at 20° C., and the storage modulus and loss modulus are displayed in straight line and dot line, respectively.
Figure 1B:
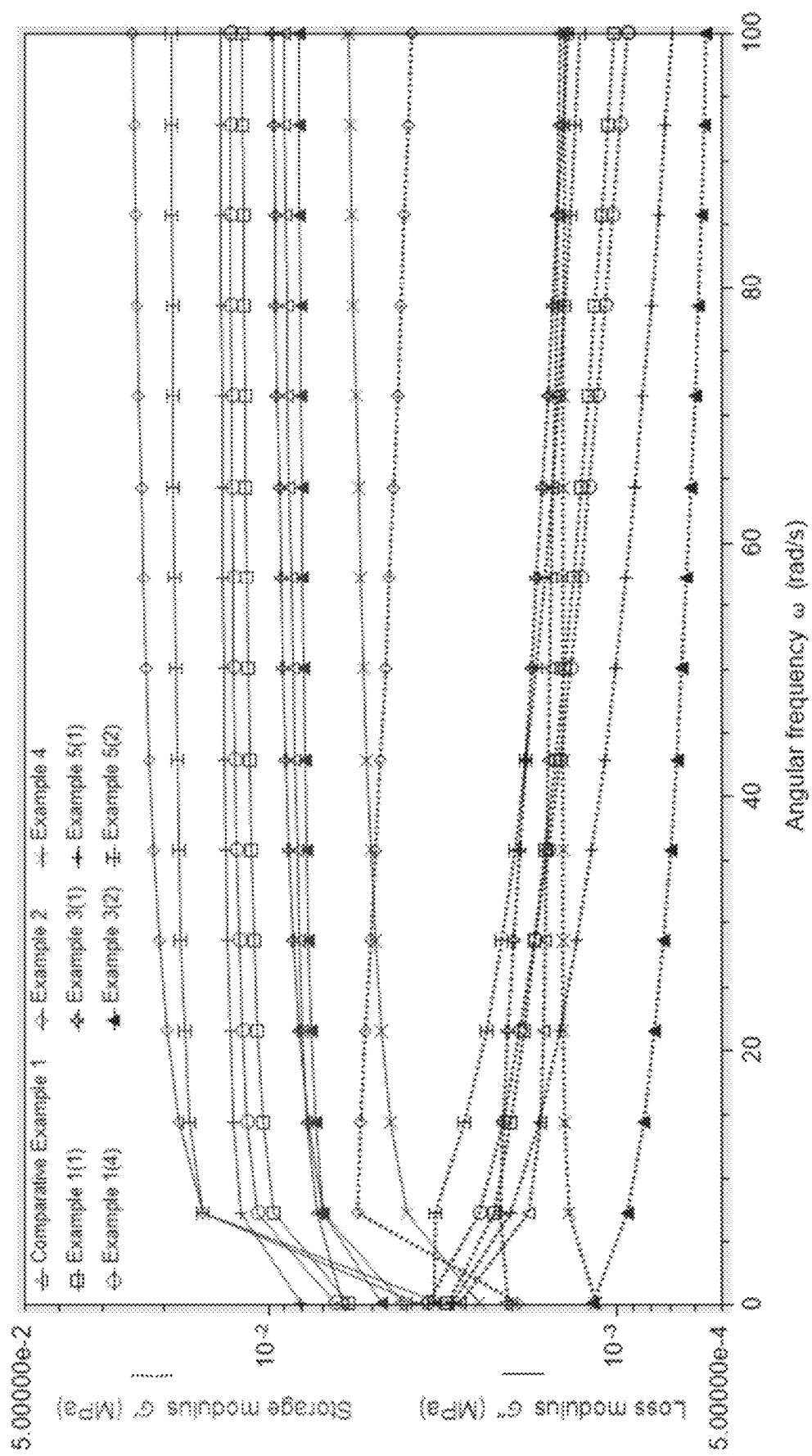
FIG. 1B illustrates the storage and loss modului of the amino acid-modified Pluronic prepared from Examples 1-5 and the unmodified Pluronic prepared in Comparative Example 1. The measurement was performed at 37° C., and the storage modulus and loss modulus are displayed in straight line and dot line, respectively.

The viscosity, sol-gel transition temperature and viscoelastic properties of the amino acid-modified Pluronic F-127 hydrogels prepared from Examples 1-5 and an unmodified counterpart of Comparative Example 1, were characterized using an HR10 rheometer (TA Instruments) equipped with a cone plate configuration and a metal cover that is to prevent solvent evaporation. The viscosity measurements were performed at a shear rate of 1.0 s$^{-1}$ with a temperature ramp of 2° C./min. The sol-gel transition temperature is defined as at a particular temperature in which the storage modulus and the loss modulus of a material are crossed with each other, which was measured in a range of 20° C. to 37° C. through oscillation mode with a temperature ramp of 2° C./min, a torque value of 100 μN·m, and a fixed frequency of 1 Hz. The viscoelastic properties were measured through frequency sweep with 1% strain at 20° C. and 37° C., respectively. The results of viscosity and sol-gel transition temperature are presented in Table 1A and 1B, respectively, and the results of viscoelastic properties are illustrated in FIG. 1A and 1B.

As shown in Table 1A, the viscosities of the hydrogels prepared from Examples 2 and 5(2) at both 25° C. and 37° C. were extremely higher than that of the Comparative Example 1, indicating that the polymer chains of the Lysine and Cysteine-modified polymers were in more complicated entanglement, where the Lysine and Cysteine residues may contribute strong interactions between polymers, amino acid residues, and water, leading to improvement on the mechanical strength of the polymer. These results provide strong evidence that the mechanical strength of a Pluronic F-127 structure can be greatly enhanced by modifying with some amino acids. In the case of the hydrogel prepared from Example 4, the viscosities at both 25° C. and 37° C. were significantly lower than that of the Comparative Example 1, suggesting that amino acid with aromatic group may hinder the chain entanglement of the modified polymer, and eventually led to an increase in polymer fluidity, which may provide other usability, such as spraying. For the hydrogels prepared from other Examples, as displayed in Table 1A, they all exhibited higher viscosities than that of the Comparative Example 1, although their viscosities were not remarkably increased like those of that prepared from Examples 2 and 5(2), these Examples still provide an insight, which is, the mechanical strength of the Pluronic F-127 may be improved when incorporated one or some amino acids into the chain-end of a Pluronic.

Table 1B demonstrates the sol-gel transition temperature of the hydrogels prepared from Examples 1-5. As shown in Table B, firstly, it was confirmed that the prepared hydrogels were all temperature sensitive, although they were all modified by different types of amino acids. Secondly, the hydrogels prepared from Examples 1-5 all presented higher sol-gel transition temperature than that of Comparative Example 1. Significantly, the hydrogels prepared from Examples 2 and 5(2) exhibited remarkably higher sol-gel transition temperature than that of Comparative Example 1, indicating more hydrogen bindings or interactions were formed between hydrogels and water, where the formation of hydrogen bindings or interactions should be attributed to the amino groups of Lysine or the thiol groups of cysteine in the polymer chains, so that the hydrophobic chains of these modified hydrogels may require higher temperature to aggregate and eventually to form solid-like gels.

The viscoelastic properties of the hydrogels prepared from Examples 1-5 and in Comparative Example 1 were investigated using rheometer to better evaluate their mechanical properties. As shown in FIG. 1A, at 20° C., larger loss modulus (G") values than storage modulus (G') values were observed for all of the hydrogels prepared from Examples 1-5, indicating all of these hydrogels exhibited sol-like properties at room temperature, which enable these hydrogels to be used for more diverse applications. As shown in FIG. 1B, at 37° C., larger storage modulus (G') values than loss modulus(G") values were observed for all of the hydrogels prepared from Examples 1-5, indicating these hydrogels all exhibited gel-like properties. Moreover, hydrogels prepared from both of Examples 2 and 5(2) presenting extremely larger storage modulus (G') values than their loss modulus(G") values, suggesting these hydrogels exhibit excellent mechanical strength. Additionally, aside from the hydrogels prepared from Examples 3(2) and 4, those of that prepared from other Examples all exhibited larger storage modulus (G') values than that of the Comparative Example 1, indicating better mechanical properties were obtained. Significantly, referring to the hydrogels prepared from Examples 2, 5(2) and in Comparative Example 1, the Lysine- and Cysteine-modified Pluronic hydrogels presented extremely larger storage modulus (G') comparing with that of the unmodified Pluronic hydrogel, indicating that unmodified Pluronic hydrogel can gain a superior reinforcement in mechanical properties after being modified with one or some amino acids. To be noted, although the hydrogels prepared from Examples 3 presenting insignificant changes in storage modulus (G') values comparing with that of the Comparative Example 1, they may still possess different mechanical strength because their viscosities were notably higher than that of Comparative Example 1. Not surprisingly, the hydrogel prepared from Example 4 exhibited notably smaller storage modulus (G') values than that of Comparative Example 1, suggesting that the hydrogel may have a weaker mechanical strength than that of the Comparative Example 1. The viscoelastic results of the prepared hydrogel were consistent with the results obtained from the viscosity measurements.

TABLE 1A

|  | Viscosity (Pa · s) (25° C.) | Viscosity (Pa · s) (37° C.) |
| --- | --- | --- |
| Example 1 (1) | 0.06 | 162.2 |
| Example 1 (4) | 1.03 | 168.1 |
| Example 2 | 11.6 | 2260.9 |
| Example 3 (1) | 0.06 | 165.8 |
| Example 3 (2) | 0.05 | 150.9 |
| Example 4 | 0.04 | 70.2 |
| Example 5 (1) | 0.06 | 160.5 |
| Example 5 (2) | 4.53 | 1378.1 |
| Comparative Example 1 | 0.08 | 90.3 |

TABLE 1B

|  | Sol-gel phase transition temperature (° C.) |
| --- | --- |
| Example 1 (1) | 30 |
| Example 1 (4) | 29 |
| Example 2 | 33 |
| Example 3 (1) | 28 |
| Example 3 (2) | 28 |
| Example 4 | 28 |
| Example 5 (1) | 27 |
| Example 5 (2) | 33 |
| Comparative Example 1 | 26 |

EXPERIMENTAL EXAMPLE 2

Measurement of Polymer Residence Time in Vitro (1) Preparation of Amino Acid-Modified Polymer Hydrogels Each of amino acid-modified Pluronic F-127 prepared from Examples 1-5 was dissolved in distilled water with a final concentration of 15% (w/v).

(2) Preparation of Comparative Example 1

An amount of Pluronic F127, was added with a quantity of distilled water to form a polymer hydrogel with a final concentration of 15% (w/v).

(3) Residence Time Measurement

In the present invention, the methodology applied to measure the residence time of the prepared polymer hydrogels refers to the U.S. Pat. No. 10,105,387.

Briefly, 1 mL of each polymer hydrogels prepared from Examples 1-5 and in Comparative Example 1, was added to an individual vial of 7 mL. Then, all the vials were placed in an incubator at 37° C. to obtain solid polymer hydrogels. After all hydrogels in each individual vial were in gel phase, 1mL of phosphate buffer solution (PBS, pH 7.4) was added thereto. Afterwards, the phosphate buffer solution on the surface layer of the prepared polymer gel was removed in a fixed time interval once a day while storing the vial in an incubator at 37° C. The residual volume of the polymer gel was observed to measure an in-vitro polymer gel residence time, and the results are demonstrated in Table 2.

As shown in Table 2, residence time of the hydrogels prepared from Examples 1 to 5 were all longer than that of Comparative Example 1, ranging from 4 to 18 days. Significantly, hydrogels prepared from Examples 2 and 5(2) showing remarkably superior gel residence time, 16 and 18 days, respectively. Comparative Example 1 was not modified with any type of amino acid, showing the shortest gel residence time, about 2 days. Therefore, Pluronic being modified with various types of amino acids was found to improve its gel residence time.

These results suggest that Pluronic hydrogel with amino acid modification increase the hydrogen bonds in the polymer chain, hydrogen bonds between the polymer chains, and hydrogen bonds between polymer chain and surrounding water, thereby, improving the ability of water-erosion resistance on the hydrogel. Moreover, Lysine- and Cysteine-modified Pluronic hydrogels provide additional concrete evidence for the improvement on the water-erosion resistance, because their amine and thiol groups tend to form hydrogen bonds or even form disulfide bonds (through thiol groups), which eventually lead to a great enhancement of the gel stability against water-erosion. As a conclusion, the hydro-structures of those modified hydrogels can be greatly strengthened by introducing one or some amino acids.

It is also worth noting, as previously described that the increases in viscosities and in storage modulus could be considered as improvements on the mechanical strength of the prepared hydrogels; contradictorily, the hydrogel prepared from Example 4 showed relatively lower viscosity and weaker mechanical strength than those of Comparative Example 1, but still exhibited longer gel residence time than that of comparative Example 1. This may be attributed to the innate property of a Tyrosine as it is a hydrophobic amino acid and is naturally repulsive to water, which may help the Tyrosine-modified Pluronic hydrogel to resist the water-erosion, thereby increasing the gel residence time.

TABLE 2

|  | Gel residence time (day) |
|---|---|
| Example 1 (1) | 4 |
| Example 1 (4) | 4 |
| Example 2 | 16 |
| Example 3 (1) | 4 |
| Example 3 (2) | 4 |
| Example 4 | 4 |
| Example 5 (1) | 4 |
| Example 5 (2) | 18 |
| Comparative Example 1 | 2 |

EXPERIMENTAL EXAMPLE 3

In Vitro Mucoadhesive Measurement (1) Preparation of Amino Acid-Modified Polymer Solutions Each of amino acid-modified Pluronic F-127 prepared from Examples 1-5 was dissolved in ultrapure water with a final concentration of 15% (w/v), and each of the polymer solutions was kept in cold until use.

(2) Preparation of Comparative Example 1

An amount of Pluronic F127 was dissolved in ultrapure water to obtain a polymer solution with a final concentration of 15% (w/v), the polymer solution was kept in cold until use.

(3) Preparation of Mucin Solution

The mucin solution was prepared by dissolving the mucin powder in ultrapure water to obtain a 15% (w/v) solution. In detail, mucin was added slowly to 100 ml ultrapure water under gentle magnetic stirring (200 rpm), in a cold water bath maintained at 4° C. At the end of the preparation, the mucin solution was stored at 4° C. until use.

(4) Preparation of Polymer-Mucin Mixtures

Each of the polymer powders prepared from Examples 1-5, and the unmodified polymer powder prepared in Comparative Example 1, were individually mixed with the prepared mucin solution (15wt%) to obtain a 15% (w/v) polymer-mucin mixture.

(5) In Vitro Mucoadhesive Determination

A rheological method was used to obtain a predictive and indirect evaluation of polymer mucoadhesion (Hassan, E E., et al., *A Simple Rheological Method for the in Vitro Assessment of Mucin-Polymer Bioadhesive Bond Strength*, Pharm Res 7, 491-495, 1990). The mucoadhesive properties of the amino acid-modified Pluronic F-127 solutions prepared from Examples 1-5, the unmodified counterpart of Comparative Example 1, the prepared mucin solutions, and the mixtures of the polymer and mucin solutions, were evaluated using an HR10 rheometer (TA Instruments) equipped with a cone plate configuration and a protective metal cover that is to prevent solvent evaporation. The rheological analysis was performed using flow mode in a shear rate of 10 s$^{-1}$ at 37° C., and each analysis was preceded by a resting time of 5 min at room temperature in order to avoid structural alteration caused by thermal shock.

This experiment is based on the evaluation of the measured viscosity of a dispersion obtained from the mixture of the amino acid modified-polymer and a solution of mucin. The degree of interaction between these two components is the measurement of the final viscosity of the mixture ($f_{final}$), which represents a parameter to an established interaction between the polymer and mucin, and that can be calculated by the following equation:

$$\eta_{final} \eta_{mixture} - (\eta_{polymer} + \eta_{miucin})$$

where:

$\eta_{mixture}$=viscosity of the mixture comprising polymer and mucin $\eta_{polymer}$=viscosity of the polymer $\eta_{mucin}$=viscosity of mucin In the case of interactions between the polymer and mucin, the value of $\eta_{final}$>0 (Mayol L., et al., *A novel poloxamers/hyaluronic acid in situ forming hydrogel for drug delivery: Rheological, mucoadhesive and in vitro release properties*, Eur J Pharm Biopharm 70(1); 199-206, 2008), and the results are displayed in Table 3.

As shown in Table 3, the mucoadhesive property of each polymers prepared from all Examples was represented with the calculated viscosity of $\eta_{final}$. Clearly, all prepared polymers exhibited a certain degree of mucoadhesive properties. Further, amino acid-modified F-127 polymers prepared from Examples 1 and 4 presenting lower values of $\eta_{final}$ than that of Comparative Example 1, while the polymers from other Examples all exhibiting significantly higher values of $\eta_{final}$, suggesting that the use of hydrophobic and aromatically hydrophobic amino acids to modify Pluronic F-127 should result in a decrease of the mucoadhesive properties to the modified polymers. These results can be attributed to the low availability of the side-chains in hydrophobic amino acids. To be more specific, in this case the side chains in hydrophobic amino acids including Leucine, Methionine, and Tyrosine (classified as aromatic amino acid but presents hydrophobic property), are less available to generate interactions (e.g., hydrogen bonds) with mucin, and thus their mucoadhesive properties are relatively weak. In contrast, polymers prepared from Examples 2 and 5 demonstrated significant strong mucoadhesions, because the polymer possesses a side-chain where an amine group (from Example 2), a hydroxyl group (from Example 5(1)), and a thiol group (from Example 5(2)), is available to form hydrogen bonds and/or disulfide bonds with mucin. As a result, these amino acid-modified polymers exhibit strong mucoadhesive properties.

TABLE 3

|  | $\eta_{mixture}$ | $\eta_{polymer}$ | $\eta_{mucin}$ | $\eta_{final}$ |
|---|---|---|---|---|
| Comparative Example 1 | 29.37 | 11.02 | 0.1295 | 18.22 |
| Example 1(1) | 26.22 | 14.28 | 0.1295 | 11.81 |
| Example 1(4) | 31.83 | 14.17 | 0.1295 | 17.53 |
| Example 2 | 103.3 | 52.47 | 0.1295 | 50.75 |
| Example 3(1) | 48.66 | 24.37 | 0.1295 | 24.16 |
| Example 3(2) | 73.00 | 45.10 | 0.1295 | 27.77 |
| Example 4 | 23.24 | 10.17 | 0.1295 | 12.94 |
| Example 5 (1) | 53.61 | 12.89 | 0.1295 | 40.59 |
| Example 5 (2) | 179.2 | 27.57 | 0.1295 | 151.5 |

EXPERIMENTAL EXAMPLE 4

Test of Adhesion Prevention Efficacy in Animal Model (1) Preparation of Amino Acid-Modified Polymer Hydrogels Each of amino acid-modified Pluronic F-127 prepared from Examples 1-4 was dissolved in distilled water to obtain a polymer hydrogel with a final concentration of 15% (w/v).

(2) Preparation of Comparative Example 1

An amount of Pluronic F127, was added with a quantity of distilled water to form a polymer hydrogel with a final concentration of 15% (w/v).

(3) Preparation of Comparative Example 2

Amino acid-modified polymers prepared from Examples 2 and 5(2), were first mixed in a weight ratio of 8:2 to obtain a polymer combination. A quantity of distilled water was subsequently added to obtain a hydrogel mixture with a final concentration of 15% (w/v).

(4) Animal Test

An animal test (abdominal wall abrasion rat model) was performed to evaluate the tissue adhesion prevention efficacy of the synthetic amino acid-modified polymer hydrogels. Herein, polymer hydrogels prepared from Examples 1(1), 2, 3, and 4 were used as the experimental groups, an unmodified counterpart prepared in Comparative Example 1 was used as a comparative group, a hydrogel combination that prepared in Comparative Example 2 was used as another comparative group, and a control group was used in which no material was applied to the surgical site.

In the animal test, 4 of male Sprague Dawley (SD) rats per group were intraperitoneally anesthetized by injecting 1 mL/Kg of mixture containing Zoletil® and Rompun® (1:1). The anesthetized rats were shaved and disinfected with povidone, and the peritoneum was opened by a 5 cm-long incision along the linea alba on the abdominal wall. A 2×2 cm$^2$ peritoneal defect, where the epidermis was peeled on the right abdominal wall, was created using scalpel. To the experimental groups, 2 mL of each amino acid-modified and unmodified Pluronic hydrogels with a concentration of 15% (w/v) were individually and uniformly applied to the injured sites, and gelation occurred in situ within 2 min. For the control group, the defects were washed with 2 mL of sterile normal saline. Finally, the peritoneum was closed with interrupted 3-0 silk sutures, and the skin was closed with 4-0 silk sutures, respectively.

At 14 days after surgery, the severity of tissue adhesions was examined in a double-blind manner according to the Hoffmann adhesion scoring system in which the score number is of 0, 1, 2 or 3, the higher in number, the more severe in tissue adhesion.

The detailed description for examination of tissue adhesion severity using the Hoffmann adhesion scoring system is provided in the following Table 4. The evaluated quantitative results of tissue adhesion severity using the Hoffmann adhesion scoring system are presented in Table 5 and can be graphically illustrated in FIG. 2, where the statistical differences between the control and experiment groups were analyzed by the Student's t-test with two-tailed calculation using Prism 7 for Mac (GraphPad Software, USA). The photographic illustrations of the tissue adhesions for control, comparative groups and experimental groups are displayed in FIGS. 3(A-E).

As shown in Table 5 (Also see FIG. 2), hydrogels prepared from Examples 1-4 all showed significant inhibition of tissue adhesions, while the hydrogel prepared in Comparative Example 1 exhibited insignificant effect on preventing tissue adhesion as compared with control group (Also See FIGS. 3(A-D)). In particular, the hydrogels prepared from Example 2 exhibited remarkably excellent efficacy in preventing tissue adhesion. These results suggest that hydrogels having longer residence time should be more sufficient to prevent tissue adhesion. In addition, by adjusting the combinations of different amino acid-modified polymers, the viscosity, mechanical strength, and mucoadhesion of these hydrogel mixtures can be controlled, and thus their residence time can be tunable, hence a hydrogel with expected efficacy in preventing tissue adhesion can be made. Accordingly, hydrogels prepared in Comparative Example 2 having the composition comprising a combination of Lysine- and Cysteine-modified polymers, which showed a gel residence time over 16 days and a remarkably superior tissue adhesion prevention efficacy in the animal test (Also See FIG. 3E).

TABLE 4

| Score | Severity |
|---|---|
| 0 | No adhesion |
| 1 | Filmy avascular adhesion |
| 2 | Vascular adhesion |
| 3 | Opaque or Cohesive adhesion |

TABLE 5

| | Score of Severity$^a$ | Results of Statistical Analysis |
|---|---|---|
| Control | 2.75 ± 0.25 | |
| Comparative Example 1 | 2.75 ± 0.25 | NS |
| Comparative Example 2 | 0 ± 0 | **** |
| Example 1(1) | 0.25 ± 0.25 | *** |
| Example 2 | 0 ± 0 | **** |
| Example 3(1) | 0.5 ± 0.5 | ** |
| Example 3(2) | 0.75 ± 0.75 | * |
| Example 4 | 0.75 ± 0.75 | * |

$^a$Mean ± SEM (n = 4);
*: $p < 0.05$;
**: $p < 0.01$;
***: $p < 0.001$;
****: $p < 0.0001$;
NS: not significant difference

EXPERIMENTAL EXAMPLE 5

Loading, Encapsulation, and Release of Pharmaceutically Active Agent (1) Preparation of PTX and Amino Acid-Modified Polymer Mixtures 12 mg of PTX were first dissolved in 8 mL of methanol. Afterwards, 1 g of each amino acid-modified polymers from Examples 2 and 5(2), was respective added to a corresponding PTX-methanol solution to obtain a mixture of PTX-amino acid-modified polymer.

(2) Preparation of Comparative Example 1

12 mg of PTX were dissolved in 8 mL of methanol. 1 g of unmodified Pluronic F-127 was added to the prepared PTX-methanol solution to form a PTX-Pluronic F-127 mixture.

(3) Drug Loading and Encapsulation

Herein, Paclitaxel is selected as a pharmaceutically active agent, which is loaded and encapsulated using thin-film hydration method (Wei Z., et al., Paclitaxel-Loaded *Pluronic P123/F127 Mixed Polymeric Micelles: Formulation, Optimization and in Vitro Characterization*, Int. J. Pharm, 376 (1), 176-185, 2009). Briefly, each of the drug and amino acid-modified polymer mixtures prepared from Examples 2, 5(2), and from Comparative Example 1, was transferred into an individual eggplant-shaped glass bottle and proceeded with rotatory evaporation for 1 hour to remove methanol. When methanol was removed, a layer of PTX-loaded polymer thin film was formed in the bottle, which was then placed in a vacuum oven at 50° C. overnight for a completed solvent removal. Each of the PTX-loaded polymer thin film was rehydrated with 8 mL of distilled water to encapsulate the PTX followed by filtration using 23 μm cellulose membrane to remove the unencapsulated PTX. Afterwards, each of the PTX-encapsulated polymers was proceeded with lyophilization to yield PTX-polymer powders for evaluation of the drug-loading capacity and drug encapsulation efficacy.

The equations for calculation of drug-loading capacity and drug encapsulation efficacy were provided as following, $$\text{Drug loading capacity} = \frac{\text{weight of the drug in micelles}}{\text{weight of the feeding polymer and drug}} \times 100\%$$

$$\text{Drug encapsulation efficacy} = \frac{\text{weight of the drug in micelles}}{\text{weight of the feeding drug}} \times 100\%$$

and the results are displayed in Table 6.

TABLE 6

| | PTX loading (%) | PTX encapsulation (%) |
|---|---|---|
| Example 2 | 1.19 | 90.4 |
| Example 5 (2) | 1.17 | 88.4 |
| Comparative Example 1 | 1.09 | 88.2 |

As shown in Table 6, it was confirmed that hydrogels prepared from both Examples 2 and 5(2) showed an improved drug-loading capacity as compared with Comparative Example 1. Further, hydrogel from Examples 2 also showed an enhanced PTX encapsulation efficacy. These results indicated that Pluronic F-127 can be greatly improved on its drug-loading capacity and encapsulation efficacy through amino acid modification.

(4) Drug Release

Herein, the drug release profile is examined using membrane-less diffusion method (Zhang L., et al., *Development and in-Vitro Evaluation of Sustained Release Poloxamer 407 (P407) Gel Formulations of Ceftiofur, J. Controlled Release*, 85 (1), 73-81, 2002). Briefly, each sample of the PTX-encapsulated polymer powders prepared from Comparative Example 1, Examples 2, and 5(2), was first placed in each corresponding beaker, and rehydrated to form a PTX-polymer hydrogel containing 20% (w/v) of amino acid-modified Pluronic; herein, the PTX-unmodified Pluronic hydrogel with a polymer content of 20% (w/v) was prepared from Comparative Example 1 and served as a comparative sample. Then, each of the prepared PTX-polymer hydrogel in a beaker was prewarmed in an incubator at 37° C. to retain a gel state. Afterwards, 25 mL of prewarmed release medium containing PBS-methanol mixed solution (90%:10%; v/v) were directly added onto the surface of each prepared PTX-polymer hydrogel, which was then placed in an incubator at 37° C. with a shaking speed of 100 rpm. At predetermined time, 1 mL of solution was taken from each beaker for examination of drug release, and 1 mL of release medium was subsequently added to remain the sink condition. The drug release tests on each prepared amino acid-modified Pluronic and on Comparative Example 1 were performed in triplicate and the drug-release data were detected by UV-Vis spectrometer in which the UV wavelength was set at 236 nm. The analyzed drug release profiles are displayed in FIGS. 4(A-C).

FIG. 4A demonstrates the PTX release profile of the hydrogel prepared from unmodified Pluronic F-127. As shown in FIG. 4A, about 50% of the encapsulated PTX was released within 24 hours, and all PTX was completely released from the unmodified Pluronic F-127 within 48 hours, showing a rapid drug release behavior. In addition, about 30% of the encapsulated PTX was released within the first 12 hours, indicating that an dumping drug release occurred.

FIGS. 4(B-C) demonstrate the PTX release patterns of the hydrogels prepared from Examples 2 and 5(2), respectively. As shown in FIGS. 4(B-C), within 120 hours, about 60% of PTX was released from the hydrogel prepared from Example 2, while 40% of PTX was slowly released from that prepared from Example 5(2), showing sustainable drug release profiles of these hydrogels. In addition, although both of the hydrogels released PTX completely within 168 hours, they still presented different drug release patterns. As the PTX-release rate of the hydrogel prepared from Example 2 showed a rapid increasing in the last 48 hours, the hydrogel prepared from Example 5(2) showed a promptly releasing of PTX in the last 24 hours. These results could be attributed to the differences of the mechanical strengths between these two hydrogels. As shown by the gel residence results of Examples 2 and 5(2) in Experimental Example 2, Lysine-modified hydrogel exhibited slightly shorter gel residence time than that of Cysteine-modified hydrogel, suggested the structure of the Lysine-modified hydrogel should collapse earlier and faster than that of Cysteine-modified hydrogel. Such a condition would facilitate the Lysine-modified hydrogel to develop internal channels faster than that of Cysteine-modified hydrogel, and the internal channels would allow the PTX to easily pass throughout the hydrogel, and thus, an earlier increased PTX-release rate would occur in Lysine-modified hydrogel as compared with Cysteine-modified hydrogel.

On the basis of our experimental results, it is confirmed that a Pluronic-based drug release system can be greatly improved on its drug loading, drug encapsulation, and drug-release sustainability by modifying Pluronic with one or some amino acids.

In summary, the present inventions have found that Pluronic with modification by one or some amino acids may: (1) enhance the mechanical strength of the polymer structure, (2) improve the fluidity of the polymer, giving it more usability in biomedical applications, (3) increase the water-erosion resistance ability, (4) increase the adhesiveness between the polymer and tissues, (5) enhance the tissue adhesion prevention ability, (6) increase the loading capacity in delivery of pharmaceutically active agents, and (7) improve the release profile in delivery of pharmaceutically active agents.

While the invention has been described in detail with reference to the aforesaid preferred embodiments, it should be appreciated that the foregoing description should not be construed as limiting the invention. Various modifications and substitutions will be apparent to those skilled in the art upon reading the foregoing contents. Accordingly, the scope of the invention should be defined by the appended claims.

What is claimed is:

1. A polymer having a structure of the following formula (I):

$$[AA-\underset{H}{N}-\underset{O}{\overset{O}{C}}]_m-POLY-[\overset{O}{C}-\underset{H}{N}-AA]_n \quad (I)$$

wherein:
POLY is a triblock copolymer of poly(ethylene oxide)-poly(propylene oxide)-poly(ethylene oxide);
m and n are independently from each other 0 or 1, wherein m and n cannot be 0 simultaneously; and
AA is an amino acid residue, where its amino group directly binds to the chain-end of the POLY to form carbamate (O—C(=O)—NH) linkage.

2. The polymer of claim 1, wherein POLY has an average molecular weight ranging from 1,000 to 20,000 Daltons.

3. The polymer of claim 1, wherein POLY is selected from the group consisting of Pluronic F-127 (PF127), Pluronic F-68 (PF68), and Pluronic L-35 (PL35).

4. The polymer of claim 1, wherein the amino acid residue is selected from the group consisting of hydrophobic amino acids, basic amino acids, acidic amino acids, aromatic amino acids, and hydrophilic amino acids.

5. The polymer of claim 4, wherein, the hydrophobic amino acid is selected from the group consisting of Glycine, Alanine, Valine, Methionine, Leucine, Isoleucine, and Phenylalanine; the basic amino acid is selected from the group consisting of Lysine, Histidine, and Arginine; the acidic amino acids is selected from the group consisting of Aspartic acid, Asparagine, and Glutamine acid; the aromatic amino acid is selected from the group consisting of Tyrosine and Tryptophan; and the hydrophilic amino acid is selected from the group consisting of Serine, Cysteine, Threonine, and Proline.

6. The polymer of claim 1, wherein POLY is a Pluronic, and AA is selected from the group consisting of Leucine, Methionine, Lysine, Aspartic acid, Asparagine, Tyrosine, Serine, and Cysteine.

7. A method of preventing postoperative tissue adhesion, comprising administering a polymer of claim 1, wherein the polymer has powder, solution, or gel form, and is applied by coating or spraying onto a wound site and the surfaces of surrounding tissues.

8. A composition comprising any one of polymer having a structure of the following formula (I):

$$[AA-\underset{H}{N}-\underset{O}{\overset{O}{C}}]_m-POLY-[\overset{O}{C}-\underset{H}{N}-AA]_n \quad (I)$$

or a combination thereof, and a pharmaceutically acceptable carrier;
wherein:
POLY is a triblock copolymer of poly(ethylene oxide)-poly(propylene oxide)-poly(ethylene oxide);
m and n are independently from each other 0 or 1, wherein m and n cannot be 0 simultaneously; and
AA is an amino acid residue, where its amino group directly binds to the chain-end of the POLY to form carbamate (O—C(=O)—NH) linkage.

9. The composition of claim 8, wherein POLY has an average molecular weight ranging from 1,000 to 20,000 Daltons.

10. The composition of claim 8, wherein any one of the polymer or combinations thereof is in an amount of 5% to 30% by weight of the composition.

11. The composition of claim 8, wherein POLY is selected from the group consisting of Pluronic F-127 (PF127), Pluronic F-68 (PF68) and Pluronic L-35 (PL35).

12. The composition of claim 8, wherein the amino acid residue is selected from the groups consisting of hydrophobic amino acids, hydrophilic amino acids, basic amino acids, acidic amino acids, and aromatic amino acids.

13. The composition of claim 12, the hydrophobic amino acid is selected from the group consisting of Glycine, Alanine, Valine, Methionine, Leucine, Isoleucine, and Phenylalanine; the basic amino acid is selected from the group consisting of Lysine, Histidine, and Arginine; the acidic amino acids is selected from the group consisting of Aspartic acid, Asparagine, and Glutamine acid; the aromatic amino acid is selected from the group consisting of Tyrosine and Tryptophan; and the hydrophilic amino acid is selected from the group consisting of Serine, Cysteine, Threonine, and Proline.

14. The composition of claim 8, wherein POLY is a Pluronic, and AA is selected from the group consisting of Leucine, Methionine, Lysine, Aspartic acid, Asparagine, Tyrosine, Serine, and Cysteine.

15. The composition of claim 8, wherein the combination is two or more of formula (I) mixed, wherein POLY is a Pluronic F-127 (PF127), and AA is selected from the group consisting of Lysine, Serine, and Cysteine.

16. The composition of claim 8, further comprising a pharmaceutically active agent.

17. The composition of claim 16, wherein the pharmaceutically active agent is selected from the group consisting of anticancer drugs, antibiotics, hemostatic agents, steroids, non-steroidal anti-inflammatory drugs, hormones, analgesics, and anesthetics.

18. A method of preventing postoperative tissue adhesion comprising administering a composition of claim 8, wherein the composition has powder, solution, or gel form, and is applied by coating or spraying onto a wound site and the surfaces of surrounding tissues.

* * * * *